United States Patent [19]

Romero-Sierra et al.

[11] 4,038,989
[45] Aug. 2, 1977

[54] SURGICAL SKIN CLOSURE

[75] Inventors: Cesar Aurelio Romero-Sierra, Bath; Joseph A. Tanner, Ottawa, both of Canada

[73] Assignee: Canadian Patents and Development Limited, Ottawa, Canada

[21] Appl. No.: 684,455

[22] Filed: May 7, 1976

[30] Foreign Application Priority Data

July 4, 1975 Canada .................................. 230780

[51] Int. Cl.² ........................................... A61B 17/08
[52] U.S. Cl. .................................. 128/335; 128/334 R
[58] Field of Search .......... 128/334 R, 334 C, 335 R, 128/335.5, 155; 24/16 PB

[56] References Cited

U.S. PATENT DOCUMENTS

| 679,993 | 8/1901 | Ross et al. ............................. 128/155 |
| 2,409,261 | 10/1946 | Dow ....................................... 128/335 |
| 2,762,371 | 9/1956 | Guio ....................................... 128/335 |
| 3,496,939 | 2/1970 | Odiaga et al. ...................... 128/334 R |
| 3,698,395 | 10/1972 | Hasson ................................. 128/335 |
| 3,926,193 | 12/1975 | Hasson ................................. 128/335 |
| 3,971,384 | 7/1976 | Hasson ................................. 128/335 |

Primary Examiner—Aldrich F. Medbery
Attorney, Agent, or Firm—Francis W. Lemon

[57] ABSTRACT

A therapeutic device for skin lesions is provided in which adhesively coated flexible strips are stuck to skin on opposed sides of the lesion, aligned to prevent lateral displacement of the skin and drawn together by flaps to close the skin over the lesion. This device allows the lesion to heal without the formation of keloids. The flaps may be pulled around the side bars of a buckle member to draw the flexible strips to close skin over the lesion, and then the flaps stuck to the flexible strips to hold the skin closing the lesion. For surgical incisions a transparent, removable cover may be on the folded back flaps, and the surgical incision made through the transparent, removable cover, markings on the strips may be used to align them, and the lesion may be closed by sticking the flaps together in face-to-face relation.

8 Claims, 13 Drawing Figures

SURGICAL SKIN CLOSURE

This invention relates to a therapeutic device for skin lesions.

It has already been proposed by Claude Kawchitch in an article "No-Scar Surgery Zip-Fastener", in The Medical Technologist, Volume 4, No. 4, April, 1974, to provide a surgical zip (slide) fastener to eliminate operation scars and close a wound quickly and securely and heal a wound in a faster manner than with conventional, surgical stitching. After the surgeon has pencilled the surgical cutting line on the skin, a foundation stage of the zip fastener in the form of a self-adhesive, translucent ribbon is stuck over the pencilled line so that the two ends of the line protrude as cutting guides. The self-adhesive, translucent ribbon, which has extra strong adhesive on its silicone-rubber underside, is filled with cellular foam and is capped with a perforated nylon top layer. Protruding hooks are provided on the nylon and are used later to attach the ribbon to a concertina spring forming the zip (slide) fastener.

With the self-adhesive ribbon stuck over the pencilled line the surgeon cuts through the self-adhesive, translucent ribbon along the pencilled line and into the flesh. When it is time to close the wound the surgeon pushes the two cut edges together and then stretches the concertina spring so that it narrows, clasps it to the nylon hooks, sticks both ends of the spring to the skin with adhesive plaster and the wound is neatly fastened together without the conventional, surgical stitching.

The surgical zip (slide) fastener presses the wound edges firmly together and so new tissues, which cause scars when conventional, surgical stitching are used, do not form.

While this proposal is undoubtedly an improvement over the conventional, surgical stitching in that the problem of unsightly scars or cicatrices is largely overcome, a problem still remains that no provision is made to avoid lateral displacement of the skin on opposing sides of the wound or lesion with the result that the skin may be displaced in this manner to a sufficient extent to crumple up. With the skin crumpled in this manner the wound or lesion takes longer to heal because new tissue growth is needed to close the wound or lesion at the crumple, and the new tissue growth at the crumple causes unsightly keloidosis.

It is an object of the present invention to provide a therapeutic device for skin lesions wherein lateral displacement of the skin on opposing sides of a lesion is avoided and, so the skin is not crumpled, thus reducing the healing time of the lesion because no new tissue growth is needed to close the lesion at a crumple, and the formation of keloids caused by the necessity of new tissue growth at a crumple is substantially avoided.

It would be desirable to provide a therapeutic device for reducing keloid formation from existing skin lesions which have been incurred, say, accidentally, rather than for a skin lesion to be made after the application of the therapeutic device by, say, a surgeon, and the surgical zip (slide) fastener conceived by Claude Kawchitch cannot be used in this manner because the ribbon is first applied to the skin and then cut, and no provision is made to adapt this device for application to the skin adjacent an existing wound.

It is a further object of the present invention to provide, in some embodiments, a therapeutic device which is particularly useful for reducing keloid formation from existing skin lesions which may have been incurred accidentally.

According to the present invention there is provided a therapeutic device for skin lesions, comprising:
 a. at least two flexible strip members with an adhesive coating on one side for securing the flexible strips to skin on opposing sides of a lesion,
 b. at least one flap member for each flexible strip and secured to a portion of that flexible strip which is intended to lie alongside the lesion,
 c. means for aligning the flaps to avoid lateral displacement of the skin on the opposing sides of a lesion to which the flexible strips are to be secured by the adhesive coatings, and
 d. means for drawing the holding the flexible strips closer to one another, in a direction extending across the lesion, after the strips have been secured to the skin on opposing sides of the lesion, to substantially close the skin over the lesion.

In the accompanying drawings which illustrate, by way of example, embodiments of the present invention.

Figure 1:
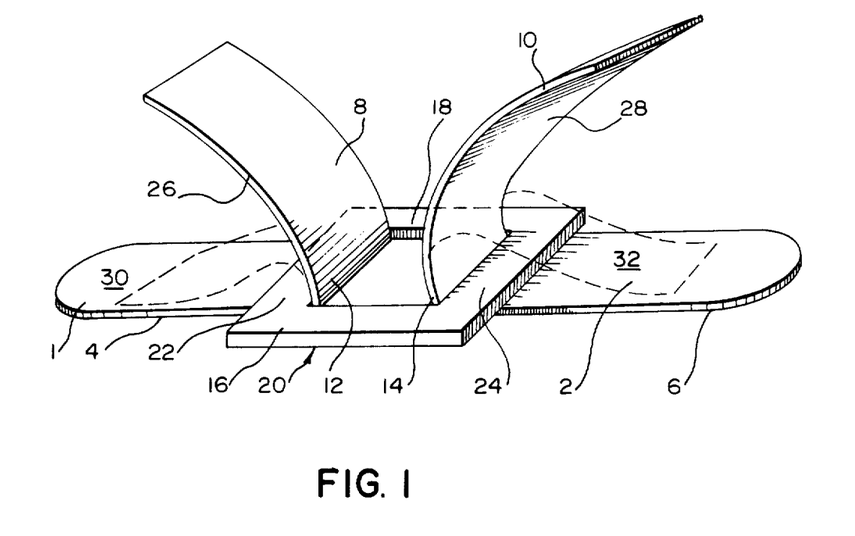
FIG. 1 is a perspective view of a therapeutic device primarily intended for use with existing skin lesions.

Referring now to FIG. 1, there is shown, a therapeutic device for skin lesions, comprising:
 a. two flexible strip members 1 and 2 with adhesive coatings 4 and 6 respectively, on one side for securing the flexible strips 1 and 2 to skin (not shown) on opposing sides of a lesion (not shown),
 b. at least one flap member, in this embodiment flaps 8 and 10 for each flexible strip 1 and 2 respectively, and secured to a portion designated 12 and 14 respectively, of that strip 1 or 2 which is intended to lie alongside the lesion,
 c. means, in the form of corner portions of side bars 16 and 18 of a buckle member 20, for aligning the flaps 8 and 10 to avoid lateral displacement of the skin (not shown) on opposing sides of a lesion (not shown) to which the flexible strips 1 and 2 are to be secured by the adhesive coatings 4 and 6 respectively, and d. means, in the form of side bars 22 and 24 of the buckle member 20, and adhesive coatings 26 and 28 on the flaps 8 and 10 respectively, for drawings and holding the flexible strips 1 and 2 closer to one another, in a direction extending across the lesion (not shown), after the strips have been secured to the skin (not shown) on opposing sides of the lesion, to substantially close the skin over the lesion.

The two flexible strips 1 and 2 are preferably of a breathable, transparent material such as cellophane, natural or synthetic rubber, polyethylene or the like having physical characteristics which are most appropriate for the skin tissue being treated. The flaps 8 and 10 may be extensions of the flexible strips 1 and 2 and may be of the same material as the flexible strips 1 and 2. Both the flexible strips 1 and 2 and the flaps 8 and 10 are more or less the same width as the gap between the side bars 16 and 18. The buckle member 20 may be moulded from a plastic material such as polyethylene.

In operation the flexible strips 1 and 2 are stuck to skin on either side of a lesion with the skin carefully aligned laterally and the side edges of the flexible strips 1 and 2 also aligned. The buckle member 20 is placed over the lesion, with the lesion in a region centrally located between the side bars 16, 18 and 22, 24 and generally parallel with the side bars 22 and 24, and the flaps 8 and 10 threaded around the side bars 22 and 24.

The flaps 8 and 10 are then pulled around the side bars 22 and 24 in a direction extending across the lesion to draw the flexible strips 1 and 2 closer to one another to substantially close the skin over the lesion without crumpling the skin. The flaps 8 and 10 are then secured to the upper surfaces 30 and 32 of the flexible strips 1 and 2 respectively so that the adhesive coatings 26 and 28 and the side bars 22 and 24 hold the flexible strips 1 and 2 in the positions where the lesion is substantially closed until the lesion has healed sufficiently for the skin to close the lesion without the aid of the flexible strips 1 and 2. The device is then removed from the skin and the wound healed with substantially no keloidosis.

It should be noted that the side bars 16 and 18 align the flaps 8 and 10 as they are drawn around the side bars 22 and 24 and thus avoid lateral displacement of the skin on opposing sides of the lession by lateral displacement of one of the flaps 8 and 10 relative to the other flap.

In other embodiments of the present invention the sides 26 and 28 of the flaps 8 and 10 respectively and the surfaces 30 and 32 of the flexible strips 1 and 2 respectively are secured together by adhesive coatings on the flexible strips 1 and 2 or by means other than an adhesive, for example these surfaces are secured together by hooks.

In yet other embodiments of the present invention one of the flaps 8 or 10 is permanently secured to the respective surface 30 or 32 prior to the application of the flexible strips 1 and 2 to the skin on either side of a lesion, and the other flap 8 or 10 is pulled around its respective side bar 22 or 24 to close the skin over the lesion and then secured to its respective surface 30 or 32.

In yet further embodiments of the present invention a central bridging member may be provided integral with the buckle member 20 and extending between the flaps 8 and 10 and joined to the side bars 16 and 18.

Figure 2:
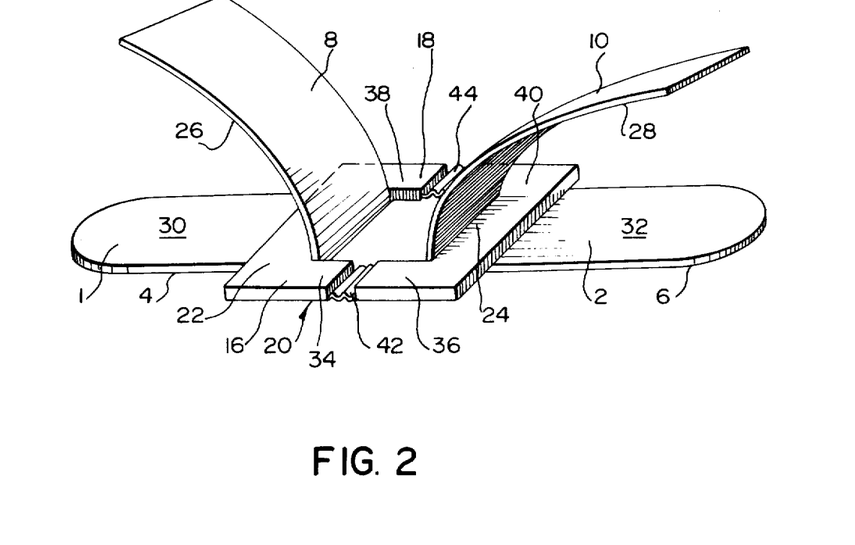
FIG. 2 is a perspective view of a different therapeutic device to that shown in FIG. 1, but which is also primarily intended for use with existing skin lesions.

In FIG. 2, similar parts to those shown in FIG. 1 are designated by the same reference numerals and the previous description is relied upon to describe them.

In FIG. 2, side bars 16 and 18 are in separate halves 34, 36, 38 and 40 and these halves are joined by wave, strip tension springs 42 and 44, in the form of undulating spring strips which assist in closing the skin over the lesion and holding the skin over the lesion. The wave, strip tension springs 42 and 44 prevent lateral displacement of the skin on opposing sides of the lesion.

The embodiment shown in FIG. 2 is used in the same manner as the embodiment shown in FIG. 1, the wave, strip tension springs 42 and 44 have the advantage that additional flexibility is provided to accommodate flexing of, for example, a limb to which the device is applied and maintain the skin closed over the lesion.

Figure 3:
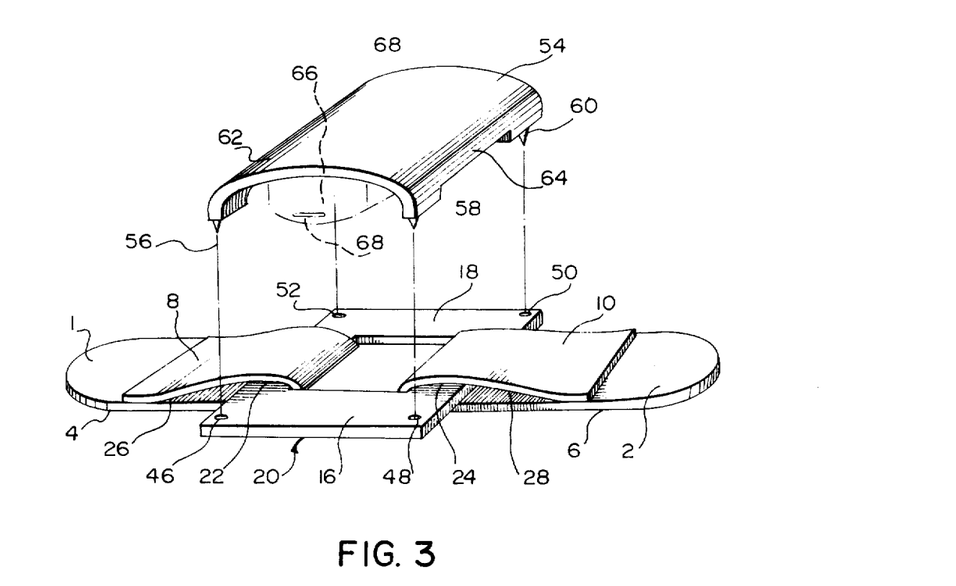
FIGS. 3 and 4 are perspective views of a similar therapeutic device to that shown in FIG. 1, and is provided with a removable cover.
Figure 4:
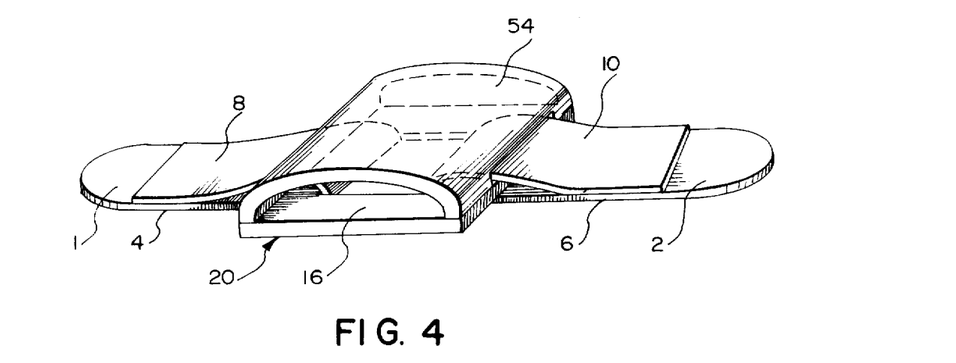

In FIGS. 3 and 4, similar parts to those shown in FIG. 1 are designated by the same reference numerals and the previous description is relied upon to describe them.

In FIGS. 3 and 4 the buckle member 20 is provided with four holes 46, 48, 50 and 52. A resilient, buckle cover member 54 is provided with four buckle engaging pins, three of which are shown and designated 56, 58 and 60, for location in the holes 46, 48, 50 and 52 to secure the buckle cover member 54 to the buckle member 20 as shown in FIG. 4. The buckle cover member 54 may conveniently be moulded from a suitable transparent plastic material and be sufficiently resilient to be sprung outwardly along the sides 62 and 64 between fingers and thumbs to locate the four pins thereon into the holes 46, 48, 50 and 52 to secure the buckle cover member 54 on the buckle member 20. The buckle cover member 54 as provided with finger gripping recesses 66 and 68 to facilitate springing the sides 62 and 64 outwardly in this manner, and the buckle member 20 may be sufficiently flexible to utilize the compression force, applied thereto in this manner by the buckle cover member 54, to close and hold the skin over the lesion.

In operation the embodiment shown in FIGS. 3 and 4 may be applied to a lesion in the same manner as the embodiment shown in FIG. 1, and the buckle cover member 54 secured to the buckle member 20 once the buckle member 20, strips 1 and 2 and flaps 26 and 28 are holding the skin to close the skin over the lesion.

Alternatively the strips 1 and 2, with the flaps 26 and 28 stuck to them and looped around the side bars 22 and 24, may be stuck to the skin on either side of the lesion and then the buckle cover member 54 sprung into position on the buckle member 20 which is sufficiently flexible for the buckle cover member 54 to close the skin over the lesion. It will be appreciated that by using the embodiment shown in FIGS. 3 and 4 in this manner there is less control over the degree of closure of the skin over the lesion, but this can be overcome by providing a number of buckle cover members 54 of different sizes, that is having different dimensions between the sides 62 and 64, so that the appropriate size of buckle cover member 54 can be chosen to close the skin over the lesion.

The buckle cover member 54 provides protection for the lesion while it is healing, and in addition a medicated absorbent pad 66, FIG. 3 (shown chain dotted) may be affixed to the under side of the buckle cover member 54 for application to the lesion through the opening in the buckle member 20. Further, the absorbent pad 66 may be impregnated with histamine and the tissue cells bounding the lesion radiated with electromagnetic radiation by electrode 68 (shown chain dotted), so that the lesion may be treated in accordance with U.S. Pat. No. 3,799,162, dated Mar. 26, 1974, "Method of Producing Collagenic Material for the Closure of Lesions", Cesar Aurelio Romero-Sierra and Joseph A. Tanner.

In other embodiments, where the flaps 8 and 10 are used to draw the flexible strips 1 and 2 to close the skin over the lesion, the sides 62 and 64 may be sprung inwardly towards one another to clip the buckle cover member 54 to the buckle member 20.

Figure 5:
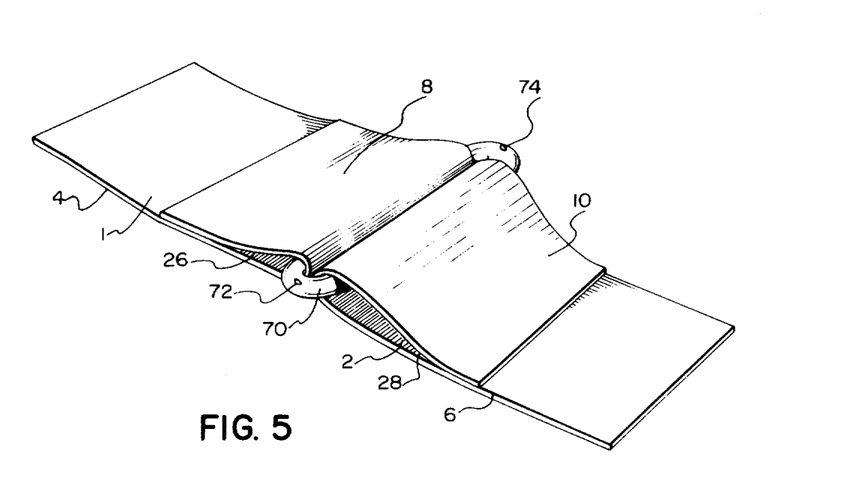
FIG. 5 is a perspective view of another, different therapeutic device to that shown in FIG. 1, but which is also primarily intended for use with existing skin lesions.

In FIG. 5 similar parts to those shown in FIG. 1 are designated by the same reference numerals and the previous description is relied upon to describe them.

In the embodiment shown in FIG. 5 an electrically conductive buckle member 70 is used provided with two holes 72 and 74 for electrical connection to a source of electromagnetic radiation (not shown).

In operation, the lesion is coated with histamine and then the embodiment shown in FIG. 5 is applied to the lesion in the same manner as the embodiment shown in FIG. 1. The buckle member 70 is then connected by the holes 72 and 74 to a source of electromagnetic radiation (not shown) and the tissue cells bounding the lesion radiated with electromagnetic energy so that lesion may be treated in accordance with the previously mentioned U.S. Pat. No. 3,799,162.

While the buckle members shown in FIGS. 1 to 5 are square they may be another rectangular shape than a square, and may be any other shape, for example, circular or oval to suit the shape of the lesion provided that the flaps are held against lateral displacement. Furthermore, any number of strips each having its own flap may be arranged side-by side in the buckle member provided the sum of the widths of the strips is sufficient to fill the buckle member adequately to prevent lateral displacement of the strips in the buckle member. Preferably when a number of strips are arranged side-by-side in the buckle member, an equal number of strips are provided around both side bars. However, it is not essential for an equal number of side-by-side strips to be provided around both side bars because, for example, one strip around one side bar may be equal to the width of two strips around the other side bar.

Figure 6:
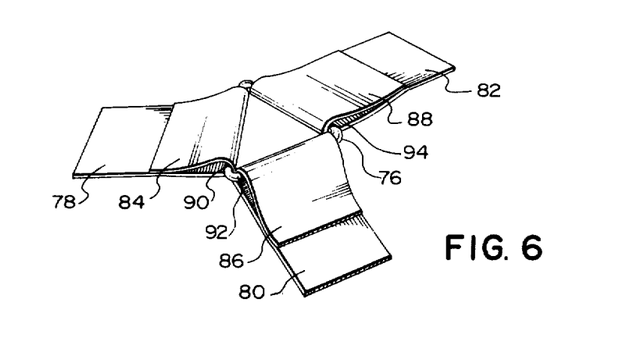
FIG. 6 is a perspective view of yet another, different therapeutic device to that shown in FIG. 1, but which is also primarily intended for use with existing skin lesions or irregular shape.

In FIG. 6 there is shown a buckle member 76 which is triangular in shape for closing irregular shaped lesions where it is necessary for skin to be drawn in three directions to close the lesion. The buckle member 76 has three flexible straps 78, 80 and 82 each provided with a flap 84, 86 and 88 respectively, and looped around a side bar 90, 92 and 94 respectively, of the buckle member 76.

The flexible straps 78, 80 and 82, and the flaps 84, 86 and 88 are adhesively coated in the same manner as the flexible straps and flaps in FIG. 1 and the lesion is closed in a similar manner by first securing the flexible straps to skin on opposing sides of a lesion, in this instance the opposing sides are the sides of a triangle, and then drawing the flaps around their respective side bar 90, 92 or 94 to close the skin over the lesion.

Figure 7:
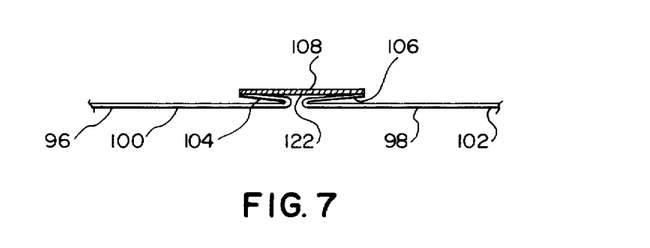
FIG. 7 is a side view of a therapeutic device for use with a skin lesion to be made by a surgeon after the device has been applied to the skin.
Figure 8:
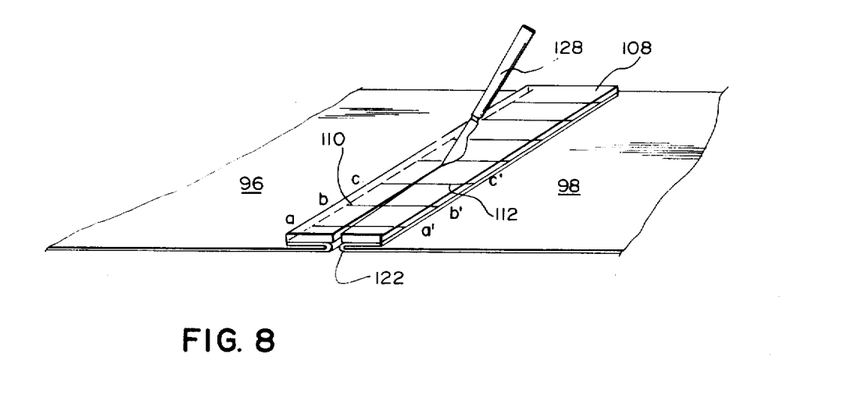
FIG. 8 is a perspective view of the therapeutic device shown in FIG. 7 applied to the skin.
Figure 9:
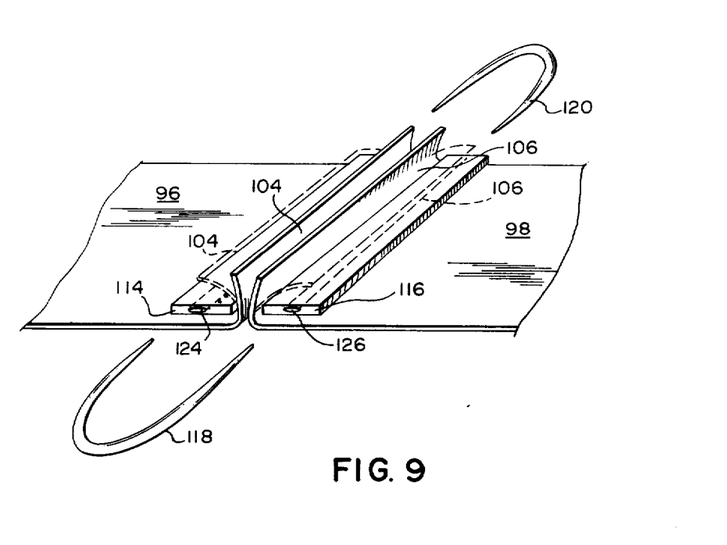
FIG. 9 is a perspective view of the therapeutic device shown in FIGS. 7 and 8 after a skin lesion has been made by a surgeon and an operation has been performed.

In FIGS. 7, 8 and 9 there is shown an embodiment of the present invention for use with a skin lesion or wound to be made by a surgeon after the device has been applied to the skin.

In FIGS. 7, 8 and 9 there is shown a therapeutic device for skin lesions, comprising:

a. at least two flexible strips, in this embodiment a pair of flexible strips designated 96 and 98, with an adhesive coating, 100 and 102 respectively on one side for securing the flexible strips to skin (not shown) on opposing sides of a lesion (not shown), b. at least one flap for each flexible strip, in this embodiment two flaps 104 and 106, and secured to a portion of that flexible strip 96 and 98 respectively, which is intended to lie alongside the lesion, c. means, in the form of a removable, transparent strip 108 on the flaps 104 and 106 and markings 110 and 112 (FIG. 8) on the flaps 104 and 106 respectively, for aligning the flaps to avoid lateral displacement of the skin on the opposing sides of a lesion to which the flexible strips 96 and 98 are to be secured by the adhesive coatings 100 and 102 respectively, and d. means, in the form of rods 114 and 116 (FIG. 9) and U-shaped staples 118 and 120 (FIG. 9), for drawing and holding the flexible strips 96 and 98 closer to one another, in a direction extending across the lesion, after the strips 96 and 98 have been secured to the skin on opposing sides of the lesion, to substantially close the skin over the lesion.

The flexible strips 96 and 98 are held spaced with a gap 122 between them by the removable strip 108 which may be of a plastic material. The rods 114 and 116 extend along the flaps 104 and 106 and have holes such as 124 and 126 at each end to receive the staples 118 and 120. The flaps 104 and 106 have an adhesive coating on their surfaces next to the removable strip 108.

In operation, a line is marked on the skin where the surgeon wishes to make an incision. The flexible strips 96 and 98, with the removable strip 108 on the flaps 104 and 106 is stuck to the skin with the marked line extending along the gap 122. As shown in FIG. 8, a surgical incision is made along the marking by means of a knife 128 cutting through the removable strip 108 into the skin.

After the operation, for which the surgical incision was made, the slit, removable strip is peeled away from the flaps 104 and 106 and the opposed marks 110 and 112 (FIG. 8), such as those designated aa', bb', and cc', are aligned. The flaps 104 and 106 are then raised to the positions shown dashed in FIG. 9 and the rods 114 and 116 are placed on each side of the flaps 104 and 106. With the opposed markings 110 and 112 still aligned the staples 118 and 120 sprung with their sides splayed apart into the holes such as 124 and 126 to secure the ends of the rods 114 and 116 together and clamp the flaps 104 and 106 together between the rods 114 and 116, thus closing the skin over the lesion. The adhesive coatings on the flaps 104 and 106 provides an extra seal in addition to the clamping force of the staples 118 and 120, and this can be further enhanced by sticking the free ends of the flaps 104 and 106 together by the adhesive coatings thereon.

In some embodiments of the present invention the adhesive coatings on the flaps 104 and 106 can be relied upon to hold the flexible strips 96 and 98 closer to one another. Such an embodiment is shown in FIGS. 10 to 12.

Figure 10:
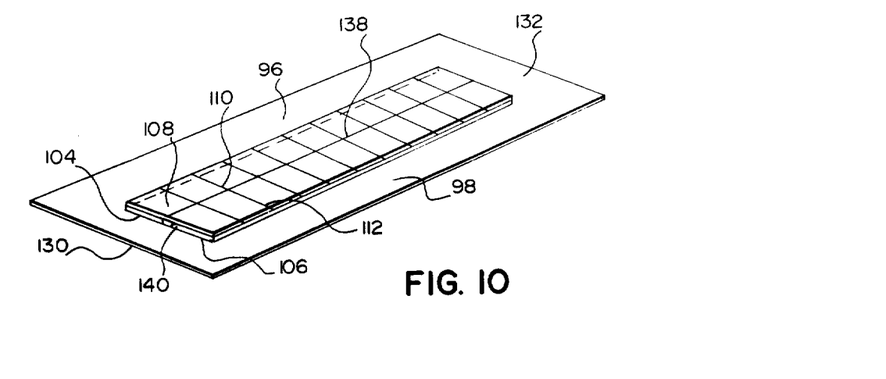
FIGS. 10 to 12 are perspective views of another therapeutic device for use with skin lesion to be made by a surgeon after the device has been applied to the skin.
Figure 11:
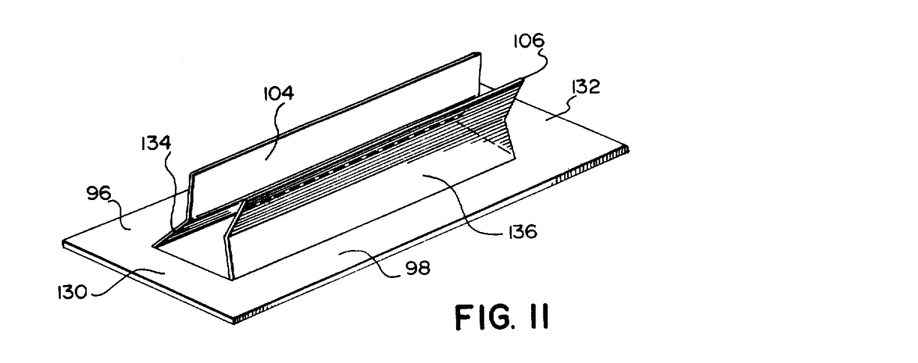
Figure 12:
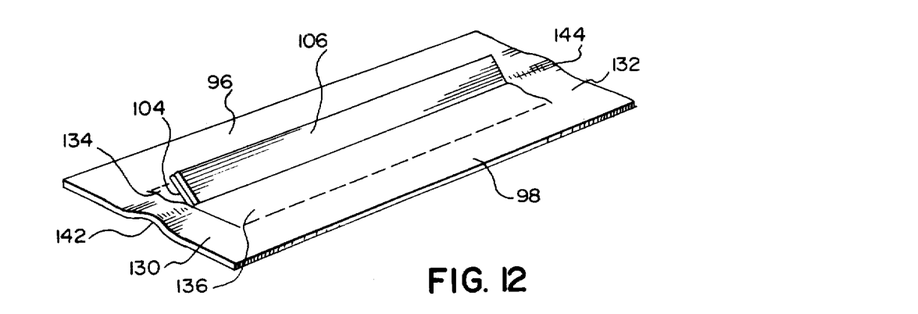

In FIGS. 10 to 12, similar parts to those shown in FIGS. 7 to 9 are designated by the same reference numerals and the previous description is relied upon to describe them.

In FIGS. 10 to 12 the flexible strips 96 and 98 are joined at their ends by end panels 130 and 132, and the flexible strips 96 and 98 are joined to the flaps 104 and 106 by panels 134 and 136 respectively. The end panels 130 and 132 have an adhesive coating on their undersides in the same manner as the flexible strips 96 and 98, and a gap 140 exists between the flexible strips 96 and 98.

In operation the flexible strips 96 and 98 and the end panels 130 and 132 are stuck to the skin in the flat condition shown in FIG. 10 after a mark 138 has been made on the skin where the incision is to be made. The incision is then made to form a lesion along the mark 138. The flaps 104 and 106 and panels 134 and 136 are then raised as shown in FIG. 11 to facilitate access to the lesion for the surgical operation.

After the surgical operation the portions of the removable strip 108 are removed, the opposed markings 110 and 112 are aligned and the flaps 104 and 106 are pressed together in face-to-face relation to draw the panels 134 and 136 closer to one another and close the gap 140 between them, thus closing the skin over the lesion made by the incision as shown in FIG. 12. This causes the end panels 130 and 132 to buckle slightly at 142 and 144 respectively. The alignment of the opposed markings 100 and 112 is facilitated by the end panels 130 and 132 restraining the flexible strips 96 and 98 against lateral displacement.

Thus in this embodiment the means for aligning the flaps to avoid lateral displacement of the skin on opposing sides of the lesion comprises the removable strip 108, the opposed markings 110 and 112 and the end panels 130 and 132. Further, in this embodiment the means for drawing and holding the flexible strips 96 and 98 closer to one another comprises the panels 134 and 136 and the adhesive coatings on the flaps 104 and 106. It will be appreciated that only one of the pair of flaps 104 and 106 need be adhesively coated for this purpose.

In a different embodiment instead of providing the opposed markings 110 and 112 the flaps are cut along the positions of the opposed markings 110 and 112 to provide a plurality of separate flaps each separately connected to one of the panels 134 and 136. When it is desired to close the skin over the lesion and opposing pairs of flaps are sequentially pressed together starting from one of the side panels 130 and 132, and then stuck together by their adhesive coatings. It will be appreciated that by sequantially pressing the flaps together in this manner the lateral alignment of skin on opposing sides of the wound is brought about by the side panel 130 of 132 from which the flaps are pressed together. This embodiment is particularly useful when it is necessary for an incision to be made that does not extend along a straight line, for example, when the incision is made along a curved path.

The devices according to the present invention for use with surgical incisions are not limited to single line incisions but may be used with multiple line incisions which intersect one another.

Figure 13:
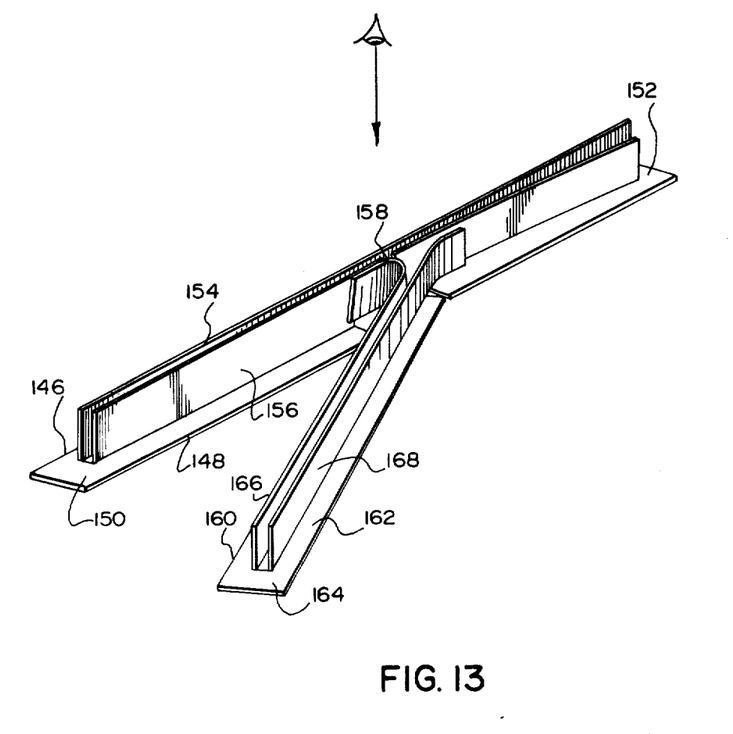
FIG. 13 is a perspective view of a therapeutic device for use with a Y-shaped skin lesion to be made by a surgeon after the device has been applied to the skin.

In FIG. 13 there is shown a therapeutic device for use with incisions made to produce a Y-shaped lesion. This device functions in a similar manner to the one shown in FIGS. 10 to 12 except that because the skin that lies between the lesions is to be peeled back for the operation it is not necessary to provide the panels 134 and 136 shown in FIGS. 10 to 12.

In FIG. 13 adhesive coated flexible strips 146 and 148 are joined by adhesive coated end panels 150 and 152 and have adhesive coated flaps 154 and 156 respectively. The flexible strip 148 and flap 156 are cut away to form a gap at 158. Adhesive coated flexible strips 160 and 162 are joined by an adhesive coated end panel 164 and have adhesive coated flaps 166 and 168 respectively. The flaps 166 and 168 are stuck by their adhesive coatings to portions of the flap 156 on each side of the gap therein at 158. The flaps 154, 156, 166 and 168 are each provided with markings in the same manner as the flaps 104 and 106, FIG. 10.

In operation the surgeon marks the skin along the path that the Y-shaped incision is to be made, and then applies the device with the flaps 154, 156, 166 and 168 covered by removable, transparent strips similar to strip 108, FIGS. 7 and 10. The surgical incisions are made in the same manner as described with reference to FIG. 10 and after the surgical operation the removable transparent strips are removed, the markings on the flaps 154 and 156 are aligned and the flaps 154 and 156 pressed and stuck together starting from one of the end panels 150 and 152. The markings on the flaps 166 and 168 are then aligned and then these flaps are pressed and stuck together starting from the end panel 164. As in the embodiment described with reference FIGS. 10 to 12 the pressing of the flaps 154, 156 and 166, 168 together closes the skin over the lesion.

It will be appreciated that instead of providing markings on the flaps 154, 156, 166 and 168 these flaps may be cut into a number of flaps which are sequentially stuck together in the manner described with reference to FIGS. 10 to 12.

The embodiment shown in FIG. 13 may be used for any surgical operation where incisions are made along intersecting lines, for example, it may be used for operations where surgical incisions are made along two parallel lines which intersect and cross a surgical incision made along another line covered by additional adhesive coated flexible strips with flaps and covered by a removable, transparent strip.

We claim:

1. A therapeutic device for skin lesions, comprising:
   a. at least two flexible strip members with an adhesive coating on one side for securing the flexible strips to skin on opposing sides of a lesion,
   b. at least one flap member for each flexible strip and secured to a portion of that flexible strip which is intended to lie alongside the lesion,
   c. means for aligning the flaps to avoid lateral displacement of the skin on the opposing sides of a lesion to which the flexible strips are to be secured by the adhesive coatings,
   d. means for drawing and holding the flexible strips closer to one another, in a direction extending across the lesion, after the strips have been secured to the skin on opposing sides of the lesion, to substantially close the skin over the lesion, and wherein the improvement comprises:
   e. a rectangular shaped buckle member having two opposite side bars around which the flaps are looped and corner portions, and
   f. means for securing the looped ends of the flaps to their respective flexible members whereby,
   g. the corner portions form said means for aligning the flaps, and the side bars together with the means for securing the looped ends of the flaps to their respective flexible members form said means for drawing and holding the flexible strips closer to one another.

2. A device according to claim 1, wherein the buckle member is in two halves, each half containing one of the side bars around which some of the flaps are looped, and further comprising wave, strip tension springs joining the ends of the two buckle halves together.

3. A therapeutic device for skin lesions, comprising:

a. at least two flexible strip members with an adhesive coating on one side for securing the flexible strips to skin on opposing sides of a lesion,
b. at least one flap member for each flexible strip and secured to a portion of that flexible strip which is intended to lie alongside the lesion,
c. means for aligning the flaps to avoid lateral displacement of the skin on the opposing sides of a lesion to which the flexible strips are to be secured by the adhesive coatings, and
d. means for drawing and holding the flexible strips closer to one another, in a direction extending across the lesion, after the strips have been secured to the skin on opposing sides of the lesion, to substantially close the skin over the lesion,
e. a buckle member having at least two side bars around which the flaps are looped and corner portions, and,
f. means for securing the looped ends of the flaps to their respective flexible members, whereby
g. the corner portions form said means for aligning the flaps, and the side bars together with the means for securing the looped ends of the flaps to their respective flexible members form said means for drawing and holding the flexible strips closer to one another, and wherein the improvement comprises:
h. a resilient, buckle cover member having a plurality of buckle engaging pins, and corresponding holes in the buckle member to the buckle engaging pins on the resilient, buckle cover member, whereby,
i. the resilient, buckle cover member may be sprung outwardly to locate the buckle engaging pins in the holes in the buckle member.

4. A device according to claim 3, which includes a medicated, absorbent pad, and the medicated absorbent pad is secured to the flexible, buckle cover member to extend into an opening in the buckle member and into contact with a lesion, once the flexible, buckle cover member is secured to the buckle member.

5. A therapeutic device for skin lesions, comprising:
a. at least two flexible strip members with an adhesive coating on one side for securing the flexible strips to skin on opposing sides of a lesion,
b. at least one flap member for each flexible strip and secured to a portion of that flexible strip which is intended to lie alongside the lesion,
c. means for aligning the flaps to avoid lateral displacement of the skin on the opposing sides of a lesion to which the flexible strips are to be secured by the adhesive coatings, and
d. means for drawing and holding the flexible strips closer to one another, in a direction extending across the lesion, after the strips have been secured to the skin on opposing sides of the lesion, to substantially close the skin over the lesion, and wherein the improvement comprises:
e. the flaps are paired and are folded back on the flexible strips, said means for aligning the flaps to avoid lateral displacement of the skin comprises corresponding markings on the flaps, and a transparent, removable cover on the flaps securing the strips with a gap between them.

6. A device according to claim 5, wherein said means for drawing and holding the flexible strips closer to one another comprises rods extending along the flaps and having holes at each end, and U-shaped staples which have been sprung with their sides splayed apart into the holes in the rods to clamp the flaps together.

7. A device according to claim 5, wherein said means for aligning the flaps to avoid lateral displacement of the sking further comprises adhesively coated end panels joining the ends of the flexible strip and for securement to the skin by the adhesive coatings.

8. A device according to claim 5, wherein said means for drawing and holding the flexible strips closer to one another comprises an adhesive coating on at least one of the flaps for securing the flaps together in face-to-face relation.

* * * * *